United States Patent
Piron et al.

(10) Patent No.: US 10,052,068 B2
(45) Date of Patent: Aug. 21, 2018

(54) TIP TRACKING APPARATUS FOR MEDICAL PROCEDURES

(71) Applicant: Synaptive Medical (Barbados) Inc., Bridgetown (BB)

(72) Inventors: Cameron Piron, Toronto (CA); Josh Richmond, Toronto (CA); Gal Sela, Toronto (CA)

(73) Assignee: Synaptive Medical (Barbados), Inc., Bridgetown (BB)

( * ) Notice: Subject to any disclaimer, the term of this patent is extended or adjusted under 35 U.S.C. 154(b) by 281 days.

(21) Appl. No.: 14/331,522

(22) Filed: Jul. 15, 2014

(65) Prior Publication Data

US 2016/0015468 A1    Jan. 21, 2016

(51) Int. Cl.
| A61B 5/00 | (2006.01) |
| A61B 5/06 | (2006.01) |
| A61B 17/00 | (2006.01) |
| A61B 90/00 | (2016.01) |
| A61B 34/20 | (2016.01) |

(52) U.S. Cl.
CPC ............ *A61B 5/6847* (2013.01); *A61B 5/064* (2013.01); *A61B 5/067* (2013.01); *A61B 34/20* (2016.02); *A61B 90/39* (2016.02); *A61B 2017/00734* (2013.01); *A61B 2034/2051* (2016.02); *A61B 2034/2055* (2016.02); *A61B 2034/2065* (2016.02); *A61B 2090/3735* (2016.02); *A61B 2090/397* (2016.02); *A61B 2090/3945* (2016.02); *A61B 2090/3983* (2016.02); *A61B 2562/0261* (2013.01)

(58) Field of Classification Search
CPC .................................................. A61B 5/6847
USPC ........................................................... 600/424
See application file for complete search history.

(56) References Cited

U.S. PATENT DOCUMENTS

| 5,700,262 A * | 12/1997 | Acosta ................. A61B 18/148 606/48 |
| 6,272,371 B1 * | 8/2001 | Shlomo ................. A61B 34/20 128/899 |
| 6,612,992 B1 * | 9/2003 | Hossack ................. A61B 8/12 600/467 |
| 8,649,847 B1 * | 2/2014 | Park .................. A61M 25/0158 600/433 |
| 2003/0225329 A1 * | 12/2003 | Rossner ........................ 600/424 |

(Continued)

FOREIGN PATENT DOCUMENTS

| WO | WO 03057061 A1 * | 7/2003 | ......... A61B 5/02007 |
| WO | 2013074617 A1 | 5/2013 | |

*Primary Examiner* — Tse Chen
*Assistant Examiner* — Joanne Hoffman
(74) *Attorney, Agent, or Firm* — Marshall & Melhorn, LLC

(57) ABSTRACT

An apparatus is provided having a proximal end, a distal end, and an outer surface. The apparatus comprises a handle portion located near the proximal end of the apparatus, a supporting arm attached to the proximal end of the apparatus, the supporting arm having a tracking marker, a flexible tip portion located at the distal end of the apparatus, and a plurality of sensors located on the outer surface of the apparatus. The plurality of sensors each provides a signal representing information that is useable for determining deformation of the flexible tip portion. The apparatus may be either a sheath for covering a medical tool or the apparatus may be a medical tool.

18 Claims, 8 Drawing Sheets

(56) References Cited

U.S. PATENT DOCUMENTS

| | | | |
|---|---|---|---|
| 2005/0075562 A1* | 4/2005 | Szakelyhidi, Jr. | A61B 5/06 600/424 |
| 2005/0143689 A1* | 6/2005 | Ramsey, III | A61M 25/10 604/103.13 |
| 2005/0228274 A1* | 10/2005 | Boese | A61M 25/0105 600/433 |
| 2006/0189867 A1* | 8/2006 | Revie | A61B 90/36 600/424 |
| 2007/0161856 A1* | 7/2007 | Belson | A61B 1/00151 600/114 |
| 2008/0114254 A1* | 5/2008 | Matcovitch | A61B 5/0097 600/463 |
| 2009/0118640 A1* | 5/2009 | Miller | A61B 90/36 600/567 |
| 2009/0281545 A1* | 11/2009 | Stubbs | A61B 17/1666 606/87 |
| 2011/0230894 A1 | 9/2011 | Simaan et al. | |
| 2013/0102851 A1 | 4/2013 | Mark et al. | |
| 2013/0204165 A1* | 8/2013 | Perry | A61B 10/0045 600/587 |

\* cited by examiner

TIP TRACKING APPARATUS FOR MEDICAL PROCEDURES

TECHNICAL FIELD

The present disclosure is generally related to image guided medical procedures, and more specifically to a tip tracking apparatus for medical procedures.

BACKGROUND

The present disclosure is generally related to image guided medical procedures using a surgical instrument, such as a catheter, a biopsy needle, a fibre optic scope, an optical coherence tomography (OCT) probe, a micro ultrasound transducer, an electronic sensor or stimulator, or an access port based surgery.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO BrainPath. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body.

In the example of a port-based surgery, a straight or linear access port 12 is typically guided down a sulci path of the brain. Surgical instruments would then be inserted down the access port 12.

Optical tracking systems, used in the medical procedure, track the position of a part of the instrument that is within line-of-site of the optical tracking camera. Since the tip of the surgical instrument may be inserted within a patient, line of site to the tip of the instrument cannot always be maintained. As well, positioning the optical tracking mechanisms at the tip may be too cumbersome to be of practical use. Conventionally, the tip and orientation of the instrument is inferred through a known transformation (e.g., either measured or determined by manufactured drawings) from the visible tracked position to the tip position.

Surgical instruments are typically rigid in nature. When these rigid tools come into contact with different densities of tissues (i.e., white matter, gray matter, tumors, muscle, etc.), the tips of the instruments may deflect or flex. This flexion may not be accounted for in the determination of the tip and orientation of the instrument since the assumption of rigidity is no longer accurate. For example, in a deep brain stimulation (DBS) or biopsy procedure, a surgical instrument with a diameter of 1-2 mm may be inserted into the brain. As this instrument comes into contact with tissue of different densities and/or stiffness, flexion of the instrument may occur (e.g., the track of the instrument may be diverted causing the tip of the instrument to flex up to 5 mm or more during contact with the tissue), thus resulting in inaccuracies.

Alternately, tracking a tool that has unknown geometry from the tracked portion (e.g., a separate piece clamped onto an existing instrument) requires computer knowledge of the geometry from the tracked instrument to the tip of the tool. Other examples include surgical instruments that allow the user to deform the instruments in an arbitrary way prior to use, such as a NICO Myriad device.

Conventional surgical navigation systems may use electromagnetic (EM) sensors such as fluxgates or induction coils for tracking the tip of surgical instruments. For example, a system such as the Aurora® Electromagnetic Tracking System from Northern Digital utilizes EM sensors. These conventional systems allow for miniature sensors to be placed at the tip of the instrument, thus allowing direct tip tracking. However, these conventional instruments rely on a stable magnetic field to be generated around the tracking volume which is impractical, if not impossible in real-life surgical environments, leading to loss of position accuracy and spurious results. Other surgical instruments have incorporated Bragg Gratings on fiber optics to achieve tip deflection information. Furthermore, it is often not possible to adapt existing surgical instruments so that the tracked portion is at the desired tip of the instrument, for example if the tip delivers energy (such as a cauterizing instrument) which could affect the tracking sensor, or if the tool was manufactured without anticipating a means to allow a tracking sensor at the tip. In these cases it is more generally useful to position the tracked portion away from the tip (e.g., a separate piece clamped onto an existing instrument) and infer the tip position from the tracked position.

In another example, the present disclosure may apply to an articulated arm system where the ex-vivo position of an instrument is determined by measuring the joint angles of the arm. However, the internal tip position would still need to be determined using aspects of the present disclosure. Therefore, there is a need to provide alternate mechanisms to counter flexion in surgical instruments when performing medical procedures.

SUMMARY

One aspect of the present disclosure provides an apparatus having a proximal end, a distal end, and an outer surface. The apparatus comprises a handle portion located near the proximal end of the apparatus, a supporting arm attached to the proximal end of the apparatus, the supporting arm having a tracking marker, a flexible tip portion located at the distal end of the apparatus, and a plurality of sensors located on the outer surface of the apparatus. The plurality of sensors each provides a signal representing information that is useable for determining deformation of the flexible tip portion. The apparatus may be either a sheath for covering a medical tool or the apparatus may be a medical tool.

Another aspect of the present disclosure provides a medical navigation system. The medical navigation system comprises an apparatus having a proximal end, a distal end, and an outer surface. The apparatus has a handle portion located near the proximal end of the apparatus, a supporting arm attached to proximal end, the supporting arm having a tracking marker, a flexible tip portion located at the distal end, and a plurality of sensors located on the outer surface. The medical navigation system further has a controller at least electrically coupled to the apparatus, the apparatus transmitting data to the controller provided by the plurality of sensors, the data indicating an amount of deformation of the flexible tip portion. The apparatus may be either a sheath for covering a medical tool or the apparatus may be a medical tool.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
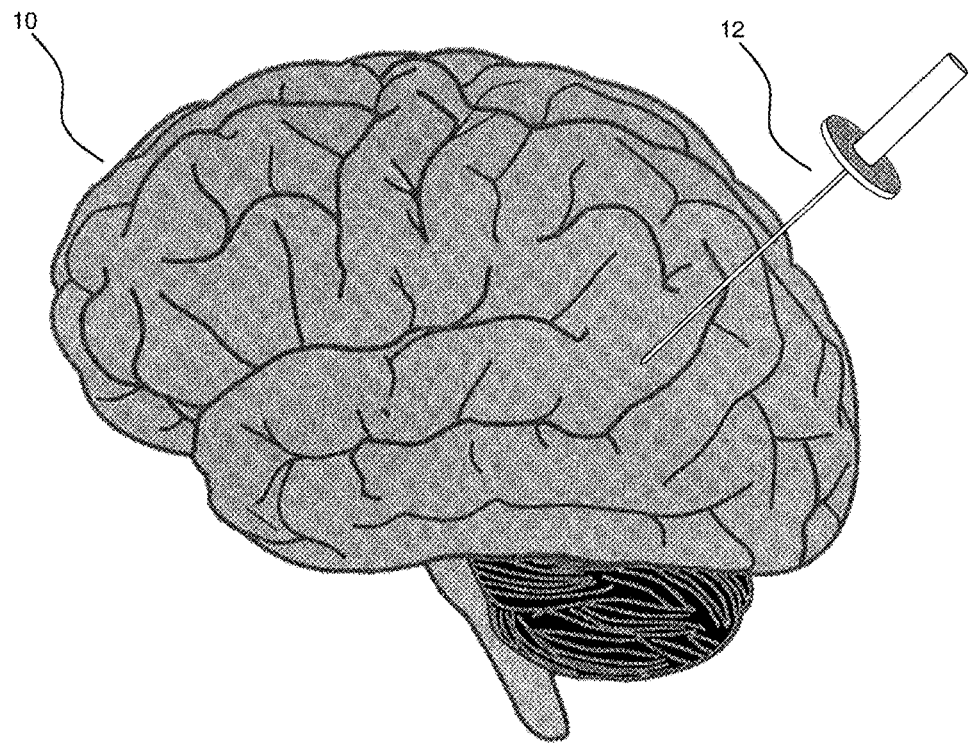
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

Figure 2:
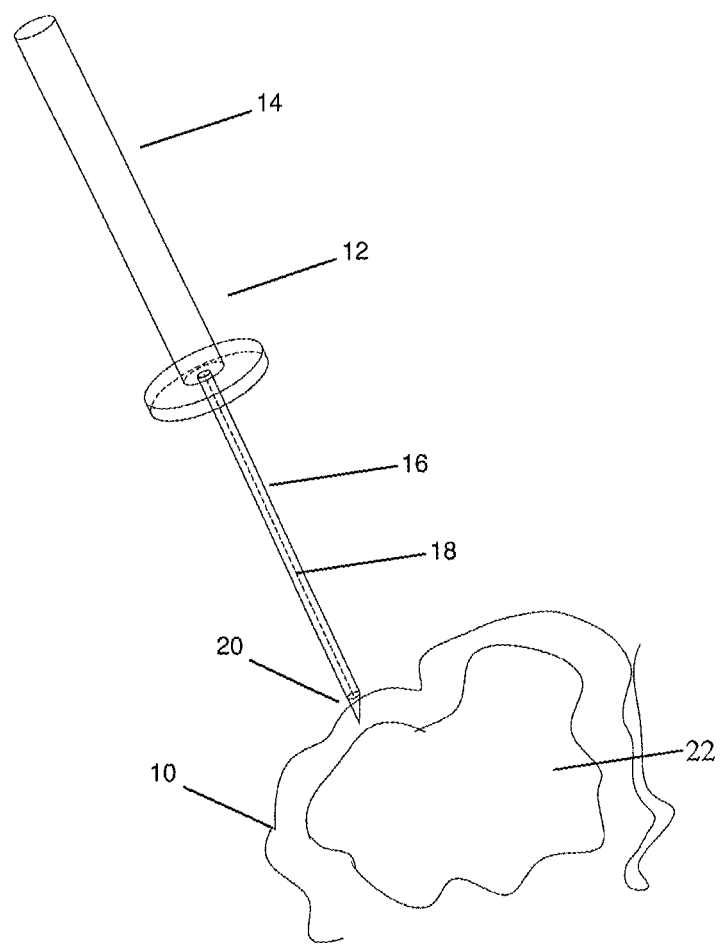
FIG. 2 illustrates the insertion of a catheter as an access port into the brain.

Referring to FIG. 2, the insertion of a catheter as an access port into the brain is shown. In FIG. 2, catheter 12 may be used as an access port positioned to navigate a human brain 10. Catheter 12 may include a handle 14 at the proximal end and a probe 18 at the distal end. In one example, the probe 18 may be substantially straight or linear; however curved probes could also be used. Probe 18 may be a resection tool, an image sensor and/or other types of sensing tools that can take measurements in different imaging modalities (e.g., ultrasound, Raman, optical coherence tomography (OCT), positron emission tomography (PET), magnetic resonance imaging (MRI), etc.).

Probe 18 may enter the brain 10 and be navigated to targeted internal tissue 22. In one example, the probe 18 may follow sulci path 20, however, due to the typically linear nature of probe 18, a linear path to targeted internal tissue 22 is usually mapped out.

Figure 3A:
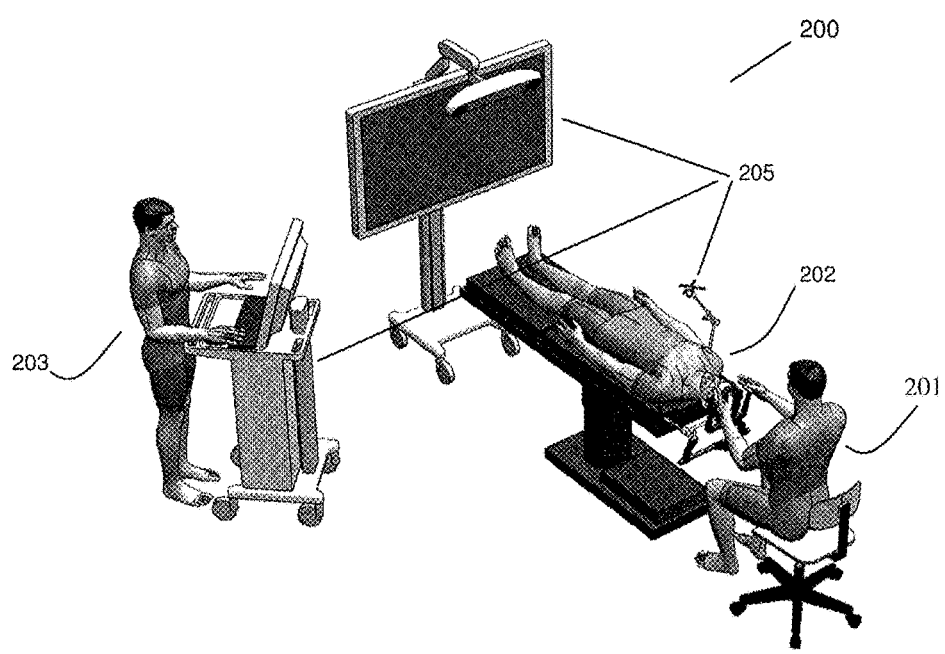
FIG. 3A shows an exemplary navigation system to support minimally invasive access port-based surgery.

Referring to FIG. 3A, an exemplary navigation system environment 200 is shown, which may be used to support navigated image-guided surgery. As shown in FIG. 3A, surgeon 201 conducts a surgery on a patient 202 in an operating room (OR) environment. A navigation system 205 comprising an equipment tower, tracking system, displays and tracked instruments assist the surgeon 201 during his procedure. An operator 203 is also present to operate, control and provide assistance for the navigation system 205.

Figure 3B:
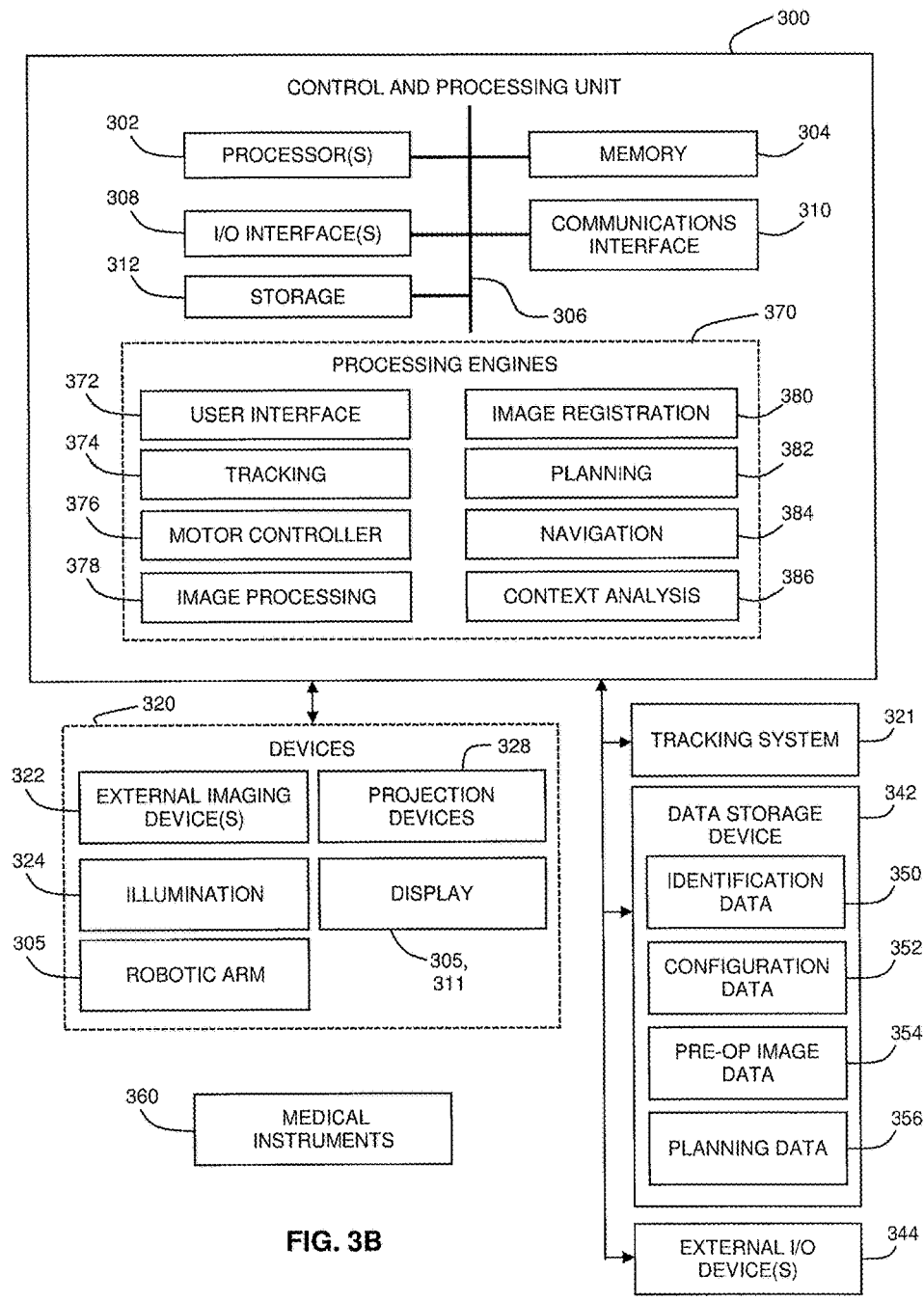
FIG. 3B is a block diagram illustrating a control and processing system that may be used in the navigation system shown in FIG. 3A.

Referring to FIG. 3B, a block diagram is shown illustrating a control and processing system 300 that may be used in the navigation system 200 shown in FIG. 3A (e.g., as part of the equipment tower). As shown in FIG. 3B, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, foot pedal, and microphone and speaker. Data storage 342 may be any suitable data storage device, such as a local or remote computing device (e.g. a computer, hard drive, digital media device, or server) having a database stored thereon. In the example shown in FIG. 3B, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3B, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3B, include one or more external imaging devices 322, one or more illumination devices 324, a robotic arm, one or more projection devices 328, and one or more displays 205, 211.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3B, in one example the processing modules 370 may be stored in the memory 304 and the processing modules may be collectively referred to as processing modules 370.

It is to be understood that the system is not intended to be limited to the components shown in FIG. 3B. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to suitable medical procedure.

Figure 4A:
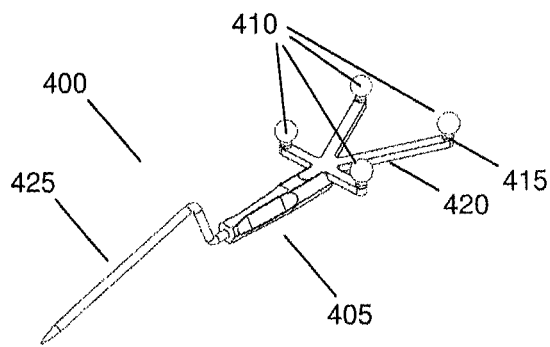
FIG. 4A and FIG. 4B illustrate exemplary pointing tools with tracking markers.
Figure 4B:
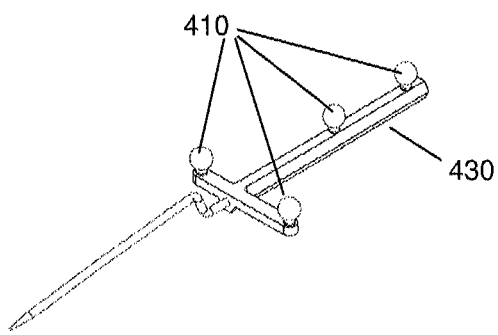

Referring to FIG. 4A and FIG. 4B, perspective views of exemplary pointing tools with fiducial or tracking markers are shown. Referring to FIG. 4A, a pointing tool 400 has a handle portion 405 and a tip portion 425. In one example, the handle portion 405 may be constructed of a rigid plastic material or stainless steel. The tip portion 425 may be atraumatic and substantially rigid and may be constructed out of a metallic material. Tracking markers 410 are placed on connectors 415 attached to supporting arm structures (or branches) 420 of pointing tool 400. Generally, a minimum of two tracking markers 410 is used to provide adequate tracking in 3D space, but three or four markers (or more) may be placed on the tool 400 for increased accuracy, depending on the design criteria of a particular application.

FIG. 4A and FIG. 4B illustrates two different orientations for the supporting arm structure 420. In FIG. 4A, supporting arm structure 420 is placed in a "star-like" configuration, whereas in FIG. 4B, supporting arm structure 430 is placed in a "inverted T" configuration. Other supporting arm structures may also be contemplated by persons skilled in the relevant arts, depending on the design criteria of a particular application.

Figure 5:
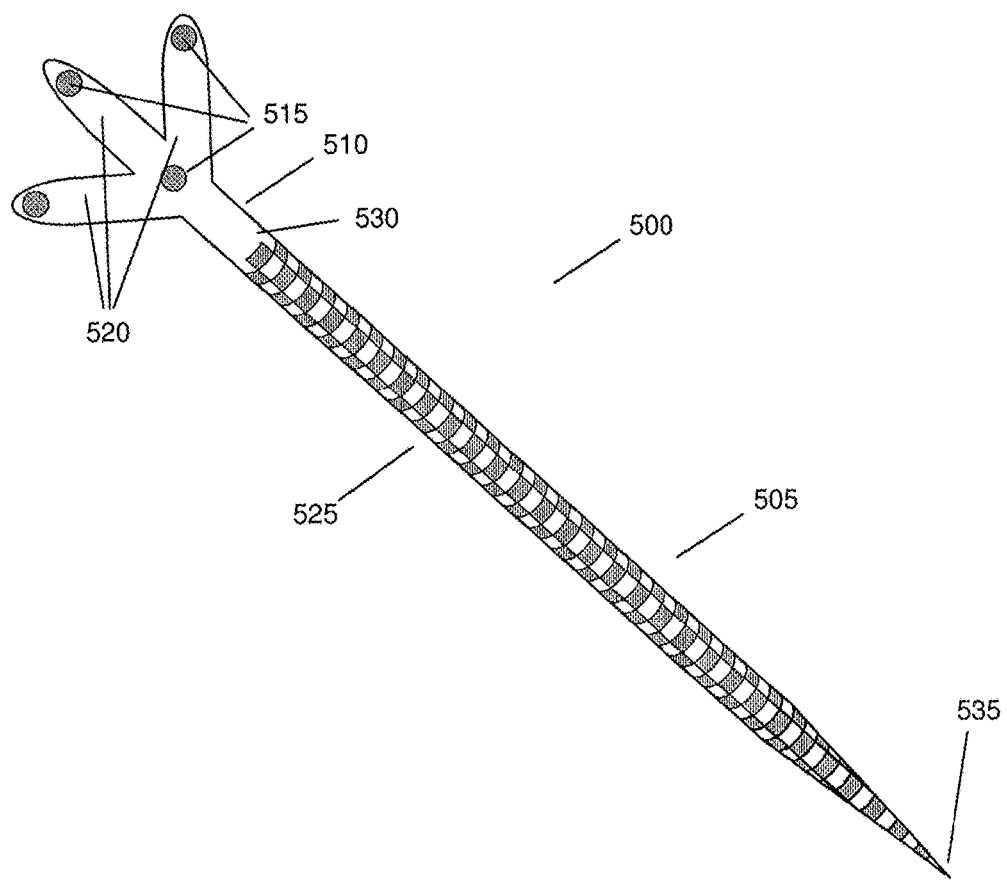
FIG. 5 illustrates an exemplary tip tracking tool.

Referring to FIG. 5, an exemplary a tip tracking tool 500 is shown. The tip tracking tool 500 may be an apparatus for use with a medical tool. The apparatus has a proximal end 530, a distal end 535, and an outer surface. The apparatus 500 further includes a handle portion 510 located near the proximal end 530 and a supporting arm 520 attached to proximal end. The supporting arm 520 may have a tracking marker 515. A flexible tip portion 505 may be located at the distal end 535 of the apparatus 500. A plurality of sensors 525 may be located on the outer surface of the apparatus 500, where the plurality of sensors 525 each provides a signal representing information that is useable for determining deformation of the flexible tip portion. In one example, the apparatus 500 may be a sheath that is placed over an existing medical instrument 360. In another example, the apparatus 500 may be a medical instrument that includes all of the features of the apparatus 500 (e.g., a medical instrument designed to integrate the features of the apparatus 500). The apparatus 500 may also be referred to through the description as the tip tracking tool 500.

The tip tracking tool 500 comprises the tip portion 505 having the proximal end 530 and the distal end 535. The distal end 535 may be a sharp point forming an atraumatic tip. Connected to the proximal end 530 of tip tracking tool 500 is a handle portion 510. Handle portion 510 includes one or more arm or branch structures 520. On each arm structure 520 is placed at least one tracking marker 515. In one example, the tracking markers 515 may be reflective spheres in the case of optical tracking systems or pick-up coils in the case of electromagnetic tracking systems. In other examples, the tracking markers 515 could be reflective spheres or disks, high contrast targets, barcodes, QR codes, or any other suitable tracking mechanism. The tracking markers 515 may be detected, for example by navigation system 205 (FIG. 3) and the respective positions of the tracking markers 515 may be inferred by the navigation software (e.g., navigation engine 384).

Active or passive tracking markers 515 may be placed on tip tracking tool 500 to determine the location of the tools by the tracking system (e.g., tracking system 321 of navigation system 205). The spheres are seen by the tracking system to give identifiable points for tracking. A tracked instrument is typically defined as a grouping of spheres defining a rigid body to the tracking system, which may be used to determine the position and pose in 3D space of a tracked instrument 360. Typically, a minimum of three spheres are placed on a tracked tool or instrument 360 to detect and define the position of the tracked instrument 360. In the examples shown in FIG. 4 and FIG. 5, four spheres are used on the apparatus 500 and 600 (FIG. 6) to track each tracked instrument 360.

The tip tracking tool 500 may have a number of additional sensors 525 located closer to the distal end 535 of the tool 500. For example, the additional sensors 535 may include a PH sensor or other suitable sensors that can provide a signal to the navigation system 205 to provide for measuring changes in the local environment. For example, the additional sensors may provide for measuring changes in tissue state during the intervention, or facilitating treatments such as chemotherapy to see how a tumour locally responds to different agents introduced in-vivo.

Referring back to FIG. 5, over the length of the tip portion 505 of tip tracking tool 500, a number of strain gauge sensors 525 may be placed. A strain gauge is a sensor that indicates the strain of a material or structure at the point of attachment. Typically, strain gauges measure the magnitude and direction in which the deflection occurs. Typically, the strain gauge includes an insulating flexible backing which supports a metallic foil pattern. The strain gauge is attached to an object (e.g., to the apparatus 500) by a suitable adhesive, one example of which is cyanacrylate. As the object (e.g., tip tracking tool 500) is deformed, the foil of the strain gauge sensors 525 that are placed in the vicinity of the apparatus 500 deformation are also deformed, causing the electrical resistance of the deformed strain gauge sensors 525 to change. The resistance change, which is usually measured using a Wheatstone bridge, is related to the strain by the quantity known as the gauge factor.

The gauge factor GF is defined as:

$$GF = \frac{\Delta R/R_G}{\epsilon}$$

where
$\Delta R$: is the change in resistance caused by strain,
$R_G$ is the resistance of the undeformed gauge, and
$\epsilon$ is strain.

As an example, for metallic foil gauges, the gauge factor GF is usually a little over 2.

For a single active gauge and three dummy resistors, the output v from the bridge is:

$$v = \frac{BV \cdot GF \cdot \epsilon}{4}$$

where
BV is the bridge excitation voltage.

Strain gauge sensors 505 on tip tracking tool 500 enable the tool to account for flexion and provides the ability to infer the position of tip at end 535 even when the tracking tool 500 is deformed. If the tip deflects, strain gauges measure the amount of deflection. In one example, foil gauges typically have active areas of about 2-10 mm$^2$ in size. With careful installation, the correct gauge, and the correct adhesive, strains up to at least 10% can be measured. While foil gauges are used as an example, organic strain gauges may also be used but the values may differ than those given above.

Strain gauge sensors 505, in combination with tracking markers 515 measure the amount of deflection, as well as, provide the 3D localization of the tip tracking tool 500 in real-time. This information (e.g., signals provided by the strain gauge sensors 525 and tracking sensors of the navigation system 205) is conveyed to the tracking system 205. The information provided by the strain gauge sensors 505 is combined with the proximal position information (e.g., signals provided by the tracking sensors of the navigation system 205 tracking markers 515) by the navigation tracking system to provide an updated representation of the deflected tip position and tool orientation of the tracking tool 500. This updated position may be used by the surgical navigation system 205 to provide a more accurate display of the tracking tool 500 position within the tissue, as overlaid on imaging data (e.g., MR, CT, PET, both pre-operative and intra-operative data). In one example, the navigation software (e.g., navigation processing engine 384 and/or tracking processing engine 374 shown in FIG. 3B) may take the rigid transform and apply the deformation signal provided by the strain gauge sensors 505 to determine the tip tracking tool 500 position.

Returning to FIG. 5, in one example strain gauge sensors 525 may include 2-3 lines of strain gauges, placed in different orientations and configurations around the tip portion 505 of tip tracking tool 500. Alternatively, lines of strain gauge sensors 525 placed in a helix configuration may be wrapped around the tip portion 505.

In another example, a flexible sheet may be wrapped around tip portion 505 where the strain gauge sensors 525 may be integrated into a flexible printed circuit. A detailed description of a process to create a flexible sheet of strain gauges is outlined in the International Publication WO2013074617, entitled "PROCESS FOR IMPRINT PATTERNING MATERIALS IN THIN-FILM DEVICES", the entirety of which is hereby incorporated by reference.

Referring back to FIG. 5, in addition to active or passive markers 515, other traditional navigation markers such as active LED and EM antennas may be incorporated onto handle portion 510 to enable tracking. In a further example, handle portion 510 may include a small display to provide feedback to the user. Handle portion 510 may also incorporate inertial sensors such as accelerometers to provide more accurate local orientation information to the tracking system.

Tip tracking tool 500 may incorporate a link to the navigation system 205 using either a wired connection (e.g., a wire connected to proximal end 530 of handle portion 510 to a navigation system, such as control and processing unit 300 that may be employed in navigation system 205) or a wireless connection. If a wireless connection is utilized, a short-range wireless receiver and transmitter for a wireless protocol, such as BLUETOOTH®, ZIGBEE®, WI-FI®, and IRDA® may be used.

Further, tip tracking tool 500 may also incorporate a wired power source, tethered to the navigation system 205 or a battery power source, such as a Lithium Ion rechargeable battery or super capacitor incorporated in the handle portion 510. In the example where the tip tracking tool 500 has a source of power, the power source may be used to power active light emitting diodes (LEDs) suitably positioned on the tip tracking tool 500 (e.g., in position of the markers 515). The use of LEDs may add to accuracy in the example where lit LED spheres are used for tracking.

Apparatus 500 may be contemplated as a sheath to be placed over surgical instrument, or a port-based surgical instrument; however other tools such as catheters, biopsy needles or flexible delivery mechanism for imaging sensors may be envisioned. These surgical instruments and associated sensors may be biocompatible and sterilizable (e.g., by Gamma radiation, for example).

Figure 6:
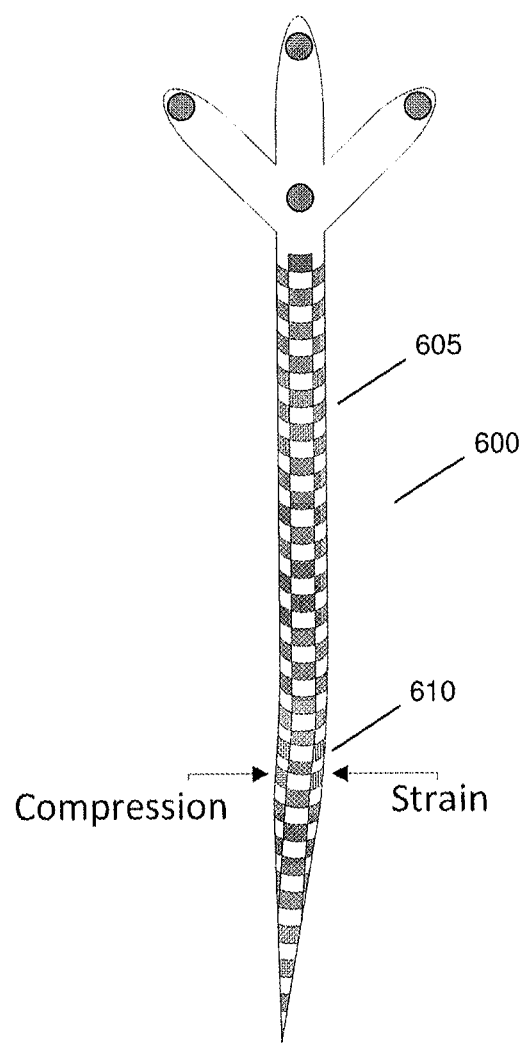
FIG. 6 illustrates a deformable tip tracking tool.

Referring to FIG. 6, a tip tracking tool 600 with a deformable tip is shown. As seen in FIG. 6, tip tracking tool 600 is similar to the tool 500 in FIG. 5, with the addition of at least one bendable joint 610 on a tip portion 605. Bendable joint 610 would enable tip tracking tool 600 to be steerable and allow for better navigation, for example down the sulci path of the brain, since the tip tracking tool 600 can adhere to the sulci path itself. Bendable joint 610 may be achieved, for example by placing a microelectromechanical system (MEMS) encoder on the joint similar to the surgical instrument outlined in US Publication US20110230894 entitled "SYSTEMS, DEVICES, AND METHODS FOR PROVIDING INSERTABLE ROBOTIC SENSORY AND MANIPULATION PLATFORMS FOR SINGLE PORT SURGERY", which is hereby incorporated by reference in its entirety.

Surgical instruments such as tip tracking tool 600 may also incorporate Fiber Bragg Gratings (FBG) sensors on fiber optics to measure tip deflection information. Fiber bundles for sensing typically consist of fibers with at least three cores. Each fiber may have Bragg-gratings co-located at regular intervals. The distance between the Bragg-gratings is determined by the required resolution for three dimensional shape tracking since the shape is inferred from deformation of the fibers as the bundle is inserted into a cavity. Fiber bundles can be affixed to the tip of the introducer. The grating wavelengths are typically measured using a multi-channel optical frequency domain reflectometer. These wavelengths are calibrated by first measuring the wavelengths with the fibers placed in a straight cavity or calibration rig made of straight channels or grooves cut into a rigid body, such as a metal block. The strain is then measured using a mathematical relationship between wavelength and strain. A minimum of three such strains is typically measured using symmetrical placement of at least three fibers. Finally, the strain can be used to infer the three dimensional shape of the fibers using mathematical constructs such the Frenet-Serret formula (reference: "Shape sensing using multi-core fiber optic cable and parametric curve solutions", Jason P. M and Matthew D. R., OPTICS EXPRESS, Vol. 20, No. 3).

The basic principle of operation normally used in a FBG based sensor system is to monitor the shift in wavelength of the returned "Bragg" signal against any changes in the measured subject. The Bragg wavelength $\lambda B$ is obtained using $$\lambda B = 2n\Lambda \quad (1)$$

where $\Lambda$ is the grating pitch and n is the effective index of core. The Bragg wavelength shifts through a change of the core effective index and the grating pitch representing varying levels of temperature and strain. The Bragg wavelength shift in response to applied strain $\varepsilon$ is obtained using:

$$\partial \lambda / \partial \varepsilon = \lambda B(1 - pe) \quad (2)$$

where pe is the effective photo-elastic coefficient. Given the Bragg wavelength $\lambda B = 1550$ nm and $pe = 0.22$ for fused silica, the strain sensitivity is calculated at 1.21 pm/$\mu\varepsilon$. In addition to tip tracking, strain gauges can be used to track other related surgical instruments, such as sheaths.

Figure 7:
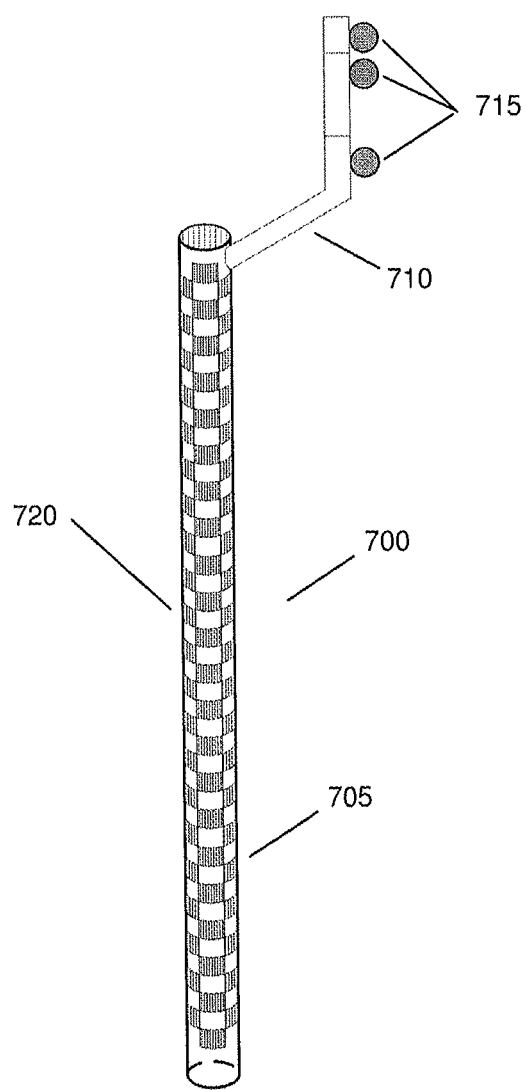
FIG. 7 illustrates a tracking sheath.

Referring to FIG. 7, an exemplary tracking sheath 700 is shown. Tracking sheath 700 comprises a substantially cylindrical barrel 705 that is hollow (tubular), forming an access port. In one example, a surgical instrument closely matching the diameter of the cylindrical barrel 705 may be inserted into the barrel 705 and the combined tool (e.g., the barrel 705 with the inserted instrument) may be used in vivo so that deflections of the surgical instrument can be measured. Along the length of the cylindrical barrel 705 of tracking sheath 700 is placed sensors 720. In one example, the sensors 720 may be strain gauge sensors. Strain gauge sensors 720 may be formed as a sheet or sleeve covering either the interior or exterior surface, or both, of cylindrical barrel 705.

At the proximal end of tracking sheath 700 is placed arm structure 710. Tracking markers 715 are connected to arm structure 710. Arm structure 710 may be releasably attached to cylindrical portion 705 by a connecting mechanism such as a clip or adjustable collar wherein arm structure 710 may be removed and placed on other cylindrical barrels with different diameters.

In one example, a measurement device may be positioned at the proximal end of the barrel 705, which may provide a signal to the control and processing unit 300 so that it may be determined how far into the barrel 705 a surgical instrument has been advanced. This would provide for a determination of how far beyond the distal end of the barrel 705 the instrument protrudes, allowing for a determination of the tip position by, for example, linearly extending the point and orientation at the end of the measured deflection of the barrel 705. In this example, an extension or retraction of the instrument within the barrel 705 could be dynamically tracked.

In another example to FIG. 7, the tracking sheath 700 may be purposefully deformable. The NICO Myriad is an example of a medical device that may be purposefully deformed by the user prior to use, after which point the tracking sheath 700 may be placed over the medical device or instrument that was bent to a desired form for use during a medical procedure. The medical device may be tracked by placing it into the tracking sheath 700 and a one-time measurement of the deformation could be obtained by slipping such a sheath onto a deformed shaft of a medical device. If it is a one-time measurement, the medical device is assumed not to bend further in use (e.g., the device is assumed to be rigid) and the tracking sheath 700 may be used to measure minor deformation occurring to the medical device during a medical procedure thereafter. An alternative one-time measurement of a deformable tool such as the Myriad is to scan the deformed tool with a structured light scanner, laser scanner or alternative 3D profiling device to register the dimensions of the deformed tool with the medical navigation system 205 prior to performing the medical procedure. An example of such a scanner is the GoScan from Creaform.

Another way to obtain a one-time measurement of the deformed instrument is to place the deformed instrument in a fixture that rigidly holds the tool's handle. A second rigid pointer tool that is tracked by the medical navigation system 205 may be run along the length of the deformed shaft from tip to the handle. The medical navigation system 205 may use this defined path as the new "true" path of the deformed instrument.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. An apparatus comprising a sheath for receiving a medical tool insertable therein, the apparatus having an apparatus proximal end, an apparatus distal end, and an apparatus outer surface, the apparatus comprising:
   a connector coupled with the apparatus proximal end, the connector supporting a tracking marker for obtaining tracking information to track position and orientation of the apparatus;
   a deformable barrel for receiving the medical tool; and
   a plurality of strain gauges located along a length of the barrel on the apparatus outer surface, from the apparatus distal end towards the apparatus proximal end, the plurality of strain gauges comprising strain gauges positioned at different axial positions and different radial positions along the length of the barrel, the plurality of strain gauges forming a grid along the length of the barrel, each strain gauge of the plurality of strain gauges providing a signal representing deformation information for determining deformation of the barrel;
   wherein the tracking marker is positioned proximal of the plurality of strain gauges;
   wherein the apparatus further comprises a communications interface for communicating the deformation information to a navigation system, the navigation system using the deformation information with the tracking information to determine position and orientation of the medical tool received in the barrel and to update navigational representation of the medical tool according to the determined position and orientation.

2. The apparatus according to claim 1, further comprising at least three tracking markers.

3. The apparatus according to claim 1, wherein the apparatus comprises a plurality of connectors coupled with the apparatus proximal end, each connector of the plurality of connectors supporting at least one tracking marker.

4. The apparatus according to claim 1,
   wherein the medical tool comprises at least one of a catheter, a needle, and a pointer, and
   wherein the barrel is configured to snugly fit the medical tool.

5. The apparatus according to claim 1,
   wherein the apparatus distal end comprises at least one of a hollow tip portion and a solid tip portion, and
   wherein the tip portion comprises a diameter within a range of 1 mm to 5 mm.

6. The apparatus according to claim 1,
   wherein the barrel comprises a flexible metal.

7. The apparatus according to claim 1, further comprising at least one power source of a wired power source and a battery.

8. The apparatus according to claim 1, further comprising at least one wireless communications interface comprising at least one of BLUETOOTH®, ZIGBEE®, WI-FI®, and IRDA®.

9. The apparatus according to claim 1, wherein the tracking marker comprises at least one of an active infrared tracking marker, an electromagnetic tracking marker, and an optical tracking marker.

10. A medical navigation system, comprising:
    an apparatus comprising a sheath for receiving a medical tool insertable therein, the apparatus having an apparatus proximal end, an apparatus distal end, and an apparatus outer surface, the apparatus comprising:
      a connector coupled with the apparatus proximal end, the connector supporting a tracking marker;
      a deformable barrel for receiving the medical tool; and
      a plurality of strain gauges located along a length of the barrel on the apparatus outer surface, from the apparatus distal end towards the apparatus proximal end, the plurality of strain gauges comprising strain gauges positioned at different axial positions and different radial positions along the length of the barrel, the plurality of strain gauges forming a grid along the length of the barrel;
    wherein the tracking marker is positioned proximal of the plurality of strain gauges;
    a tracking system for tracking the tracking marker of the apparatus in order to obtain tracking information to track position and orientation of the apparatus;

a controller operatively coupled with the apparatus and the tracking system;

wherein the controller is configured to:

receive deformation data from the apparatus, the deformation data being provided by the plurality of strain gauges, and the deformation data indicating an amount of deformation of the barrel;

receive tracking information from the tracking system;

determine position and orientation of the medical tool received in the barrel using the tracking information and the deformation data; and update navigational representation of the medical tool according to the determined position and orientation.

11. The system according to claim 10, wherein the controller is coupled with the apparatus by at least one of a wireless communications interface and a wired connection, and wherein the wireless communications interface comprises at least one of BLUETOOTH®, ZIGBEE®, WI-FI®, and IRDA®.

12. A method of fabricating an apparatus comprising a sheath for receiving a medical tool insertable therein, the apparatus having a proximal end, a distal end, and an outer surface, the method comprising:

providing a connector coupled with the proximal end of the apparatus, the connector supporting a tracking marker for obtaining tracking information to track position and orientation of the apparatus;

providing a deformable barrel for receiving the medical tool;

providing a plurality of strain gauges located along a length of the barrel on the outer surface of the apparatus, from the apparatus distal end towards the apparatus proximal end, the plurality of strain gauges comprising strain gauges positioned at different axial positions and different radial positions along the length of the barrel, the plurality of strain gauges forming a grid along the length of the barrel, each strain gauge of the plurality of strain gauges providing a signal representing deformation information for determining deformation of the barrel;

wherein the tracking marker is positioned proximal of the plurality of strain gauges; and providing a communications interface for communicating the deformation information to a navigation system, the navigation system using the deformation information with the tracking information to determine position and orientation of the medical tool received in the barrel and to update navigational representation of the medical tool according to the determined position and orientation.

13. The method according to claim 12, further comprising providing at least three tracking markers.

14. The method according to claim 12, wherein providing the connector comprises providing a plurality of connectors coupled with the proximal end of the apparatus, each connector of the plurality of connectors supporting at least one tracking marker.

15. The apparatus according to claim 1, further comprising a measurement device at the apparatus proximal end for sensing relative advancement of the medical tool relative to the barrel, wherein the sensed relative advancement is used by the navigation system together with the tracking information and the deformation information to determine the position and orientation of the medical tool.

16. The system according to claim 10, wherein the apparatus further comprises a measurement device at the apparatus proximal end for sensing relative advancement of the medical tool relative to the barrel, wherein the controller further receives information about the sensed relative advancement from the apparatus, and wherein the controller is further configured to determine the position and orientation of the medical tool by linearly extrapolating based on deflection of the barrel.

17. The method according to claim 12, further comprising providing a measurement device at the apparatus proximal end for sensing relative advancement of the medical tool relative to the barrel, wherein the sensed relative advancement is used by the navigation system together with the tracking information and the deformation information to determine the position and orientation of the medical tool.

18. The system according to claim 10, wherein the position and orientation of the medical tool are determined by applying a transformation from the tracking marker to the apparatus distal end, and further applying the deformation data after the transformation.

* * * * *